US011478001B2

(12) United States Patent
Marsh

(10) Patent No.: US 11,478,001 B2
(45) Date of Patent: Oct. 25, 2022

(54) METHODS OF ADMINISTERING A PRE-OPERATIVE CARBOHYDRATE-RICH BEVERAGE COMPOSITION

(71) Applicant: ClearFast Inc., Cardiff, CA (US)

(72) Inventor: M. Lou Marsh, Solana Beach, CA (US)

(73) Assignee: CLEARFAST INC., Cardiff, CA (US)

( * ) Notice: Subject to any disclaimer, the term of this patent is extended or adjusted under 35 U.S.C. 154(b) by 0 days.

(21) Appl. No.: 17/402,335

(22) Filed: Aug. 13, 2021

(65) Prior Publication Data

US 2021/0368829 A1 Dec. 2, 2021

Related U.S. Application Data

(62) Division of application No. 14/678,846, filed on Apr. 3, 2015, now Pat. No. 11,102,994.

(60) Provisional application No. 62/040,371, filed on Aug. 21, 2014.

(51) Int. Cl.
| | |
|---|---|
| A23L 2/52 | (2006.01) |
| A61K 9/00 | (2006.01) |
| A61K 31/522 | (2006.01) |
| A23L 2/68 | (2006.01) |
| A23L 2/60 | (2006.01) |
| A61K 45/06 | (2006.01) |
| A61K 47/26 | (2006.01) |
| A61K 9/08 | (2006.01) |
| A61K 31/07 | (2006.01) |
| A61K 31/198 | (2006.01) |

(52) U.S. Cl.
CPC .............. A23L 2/52 (2013.01); A23L 2/60 (2013.01); A23L 2/68 (2013.01); A61K 9/0056 (2013.01); A61K 9/0095 (2013.01); A61K 9/08 (2013.01); A61K 31/07 (2013.01); A61K 31/198 (2013.01); A61K 31/522 (2013.01); A61K 45/06 (2013.01); A61K 47/26 (2013.01); A23V 2002/00 (2013.01)

(58) Field of Classification Search
CPC .............................. A61P 41/00; A61K 47/183
See application file for complete search history.

(56) References Cited

U.S. PATENT DOCUMENTS

| | | | |
|---|---|---|---|
| 5,032,411 | A | 7/1991 | Stray-Gunderson |
| 5,089,477 | A | 2/1992 | Fregley |
| 5,780,086 | A | 5/1998 | Kirksey |
| 6,069,131 | A | 5/2000 | Marsh |
| 6,462,051 | B1 | 10/2002 | Nozawa |
| 2003/0003130 | A1 | 1/2003 | Okubo |
| 2006/0159829 | A1 | 7/2006 | Owen |
| 2007/0149619 | A1 | 6/2007 | Takagi |
| 2010/0080863 | A1 | 4/2010 | Sommerfeld |
| 2010/0255174 | A1 | 10/2010 | Sakai |
| 2011/0229521 | A1 | 9/2011 | Schiffrin |
| 2012/0252895 | A1 | 10/2012 | Summar |

FOREIGN PATENT DOCUMENTS

| | | | |
|---|---|---|---|
| WO | WO-9953756 A1 * | 10/1999 | ........... A61K 31/715 |
| WO | WO 2012142403 A1 | 10/2012 | |
| WO | WO 2012143403 A1 | 10/2012 | |

OTHER PUBLICATIONS

Smith (Journal of Thoracic and Cardiovascular Surgery vol. 132 pp. 58-65 published 2006). (Year: 2006).*
Reagan-Shaw (FASEBJ vol. 22 pp. 659-661 published 2007 (Year: 2007).*
Nikolajsen (British Journal of Anesthesia vol. 72 pp. 295-297. Published 1994) (Year: 1994).*
Breuer (Anesth. Analg. vol. 103 pp. 1098-1108. Published 2006) (Year: 2006).*
Kakuda (Biosci. Biotechnol. Biochem., vol. 64 pp. 287-293. Published 2000). (Year: 2000).*
Glover et al (CBS News Moneywatch Published Mar. 17, 2009). (Year: 2009).*
Clear. Dictionary.com (Year: 2020).
Crenshaw JT, Mischke A, Gilder RE., The effects of a prescribed preoperative carbohydrate-rich liquid beverage on elective surgery patients' ratings of discomfort from prolonged fasting. Abstract 05, 27th Annual Meeting of Society for Ambulatory Anesthesia, 2012.
Cynober L. Citrulline: just a biomarker or a conditional essential amino acid and a pharmaconutrient in critically ill patients? Crit Care 2013;17:122.
Fearon KCL, Ljunggvist 0, Von Meyenfeldt M, et al. Enhanced recovery after surgery: a consensus review of clinical care for patients undergoing colonic resection. Clin Nutr, 2005;24(3):466-477.
Fennelly M, Galletly DC, Purdie GI. Is caffeine withdrawal the mechanism of postoperative headache? Anesth Analg 1991;72(4):449-53.
International Search Report and Written Opinion dated Nov. 19, 2015 in PCT/US2015/045558.

(Continued)

Primary Examiner — Theodore R. Howell
Assistant Examiner — George W Kosturko
(74) Attorney, Agent, or Firm — Knobbe, Martens, Olson & Bear LLP

(57) ABSTRACT

Provided herein are methods of administering pre-operative beverage compositions to be ingested by a patient prior to administration of anesthesia or sedation in preparation for a safe induction of anesthesia or sedation in a patient before surgery. The beverage has one or more carbohydrates, wherein the total Calories available from the carbohydrates is at least about 200 and wherein the one or more carbohydrates are the sole source of significant Calories in the beverage, an acid, in a quantity sufficient to result in a pH of at least about 3.7 to about 4.5 and to enhance the shelf life and flavor of the beverage, a central nervous system (CNS) stimulant that is also a cerebro-vasoconstrictor, a sweetener, and water. The beverage composition, when ingested at least about two hours prior to administration of anesthesia or sedation is effective to relieve one or more symptoms associated with prolonged fasting.

20 Claims, No Drawings

(56) References Cited

OTHER PUBLICATIONS

Jones C. Badger SA, Hannon R. The role of carbohydrate drinks in preoperative nutrition for elective colorectal surgery. Ann R Coll Surg Engl, 2011;93(7):504-07.

Juneja LR, Chu D-C, Okubo, T, et al. L-theanine—a unique amino acid of green tea and its relaxation effects in humans. Trends Food Sci &Tech, 1999;10:199-204.

Kakuda T, Nozawa A, Unno T, et al. Inhibiting effects of theanine on caffeine stimulation evaluated by EEG in the rat. Biosci Biotechnol Biochem 2000;64:287-93.

Kim et al., (Free Radical Biology vol. 47 pp. 1601-1610 published 2009) (Year: 2009).

Kimura K, Ozeki M, Juneja LR, Ohira H. L-Theanine reduces psychological and physiological stress responses. Biol Psychol. 2007;74(1):39-45.

Lassen K, Soop M, Nygren J, et al. Consensus Review of Optimal Perioperative Care in Colorectal Surgery. Enhanced Recovery After Surgery (ERAS) Group Recommendations. JAMA Surgery, 2009;144(10):961-969.

Ljungqvist O. Jonathan Woods Lecture 2011: Insulin Resistance and enhanced recovery after surgery. J Parent Ent Nutr, 2012:36(4):389-98.

Moinard C, Nicolis I, Neveux N, et al. Dose-ranging effects of citrulline administration on plasma amino acids and hormonal patterns in healthy subjects: the Citrulose pharmacokinetic study. Br J Nutr, 2008;99:855-62.

National Headache Foundation Jul. 24, 2009 (Year: 2009).

Nikolajsen L, Larsen KM, Kierkegaard 0. Effect of previous frequency of headache, duration of fasting and caffeine abstinence on perioperative headache. Br J Anaesth. 1994;72(3):295-7.

Osowska S, Mainard C, Neveux N, e al. Citrulline increases arginine pools and restores nitrogen balance after massive intestinal resection. Gut, 2004;53:1781-6.

Peters JH, Beishuizen A, Keur MB, et al. Assessment of small bowel function in critical illness: potential role of citrulline metabolism. J Intensive Care Med, 2011;26:105-10.

Reagan Shaw et al FASEB J vol. 22 pp. 659-661 (2007) (Year: 2007).

Schwedhelm E, Maas R, Freese R, et al. Pharmacokinetic and pharmacodynamic properties of oral L-citrulline and L-arginine: impact on nitric oxide metabolism. Br J Clin Pharmacol, 2007;65(1):51-59.

Shapiro RE. Caffeine and headaches. Curr Pain Headache Rep. 2008;12(4):311-5.

Tamura T, Tomoaki Y, Hiroyuki K, et al. Oral carbohydrate loading with 18% carbohydrate beverage alleviates insulin resistance. Asia Pac J Clin Nutr, 2013;22:48-53.

Ware LB, Magarik JA, Wickersham N, et al. Low plasma citrulline levels are associated with acute respiratory distress syndrome in patients with severe sepsis. Crit Care, 2013;17:R10.

Yagmurdur H, Gunal S, Yildiz H, et al. The effects of carbohydrate-rich drinks on perioperative, discomfort insulin response and arterial pressure in spinal anesthesia. J Res Med Sci, 2011;10(11):1483-89.

* cited by examiner

METHODS OF ADMINISTERING A PRE-OPERATIVE CARBOHYDRATE-RICH BEVERAGE COMPOSITION

CROSS-REFERENCE AND PRIORITY TO RELATED APPLICATIONS

This application is a Divisional Application of U.S. application Ser. No. 14/678,846, filed Apr. 3, 2015, which claims priority to U.S. Provisional Patent Application No. 62/040,371, filed Aug. 21, 2014, the contents of which are hereby expressly incorporated by reference in their entireties.

BACKGROUND OF THE INVENTION

Field of the Invention

The subject relates to the formulation of a special clear-liquid beverage composition designed to be administered to a patient prior to surgery or invasive diagnostic procedure, e.g., colonoscopy, cardiac catheterization, etc., to reduce the risk of multiple pre-operative, intra-operative and post-operative complications.

DESCRIPTION OF THE RELATED ART

The subject of pre-operative patient hydration and nutrition remains controversial in the world of surgery and anesthesia despite several significant evidence-based conclusions in that arena. That data have prompted the American Society of Anesthesiologists (ASA®) to issue practice guidelines in 1999 (the "1999 ASA® Guidelines") for the fasting of healthy patients undergoing elective surgery. The guidelines endorsed the concept of allowing these patients to consume protein-free and fat-free clear liquids up to two hours prior to surgery.

In 2011, the ASA® updated its 1999 Guidelines: 1) it upheld the 2-hour clear liquid fast; 2) it directed its members not only to hydrate, but also to nourish their patients pre-operatively, "to decrease the risk of dehydration and hypoglycemia from prolonged fasting"; 3) it recommended that anesthesiologists enhance "the quality and efficiency of anesthesia care . . . by increased patient satisfaction"; and 4) it advocated "strongly . . . that verification of patient compliance with the fasting requirements should be assessed at the time of the procedure."

Over the last several years, a new paradigm of peri-operative patient care, the Enhanced Recovery After Surgery (ERAS®) Protocol, has emerged in Europe and the UK, and later entered the US (Lassen, Soop, Nygren, et al; Fearon, Ljungqvist, Von Meyenfeldt, et al). The Protocol consists of at least 17 evidence-based care elements that, when implemented, have reduced the incidence of several post-operative complications with the results of reduced length of stays (LOS) in and re-admissions to hospitals. Pre-operative loading with multiple servings of carbohydrate-rich beverages (minimally, 12.5% concentration of complex carbohydrates) up to 2 hours before anesthesia puts the patients into a metabolically fed state. Such loading was found to be an independent predictor of post-operative clinical outcomes, including reduction of post-operative nausea and vomiting (PONV). Further, it was viewed as beneficial in the reduction of the post-operative insulin resistance that is seen in both non-diabetics and diabetics and that leads to post-operative hyperglycemia and consequent surgical wound infections, muscle weakness and other complications that delay or impair recovery from surgery (Ljungqvist; Yagmurdur, Gunal, Yildiz, et al; Jones, Badger, Hannon; Tamura, Tomoaki, Hiroyuki, et al).

In truth, fasting from midnight for healthy patients undergoing elective procedures is a dated practice that is neither evidence based nor proven to be beneficial. On the contrary, the practice may be placing patients at risk, unnecessarily, for the very consequences that inspired the fasting rule: regurgitation and aspiration. At the very least, for many patients, it is contributing to a difficult and uncomfortable pre-operative experience.

SUMMARY OF THE INVENTION

Provided herein are beverage compositions to be ingested by a patient prior to administration of anesthesia or sedation comprising: a) one or more carbohydrates, wherein the total Calories available from the carbohydrates is at least about 200 and wherein the one or more carbohydrates are the sole source of significant Calories in the beverage; b) an acid, in a quantity sufficient to result in a pH of at least about 3.7 to about 4.5 and to enhance the shelf life and flavor of the beverage; c) a central nervous system (CNS) stimulant that is also a cerebro-vasoconstrictor; and d) water, wherein the beverage composition, when ingested at least about two hours prior to administration of anesthesia or sedation is effective to relieve one or more symptoms associated with prolonged fasting. Also provided herein are beverage containers that may comprise a serving of the beverage compositions disclosed herein. Further provided herein are methods of using the pre-operative beverage compositions disclosed herein in preparation for the induction of anesthesia or sedation in a patient before surgery.

The present disclosure may be summarized as relating to the following embodiments:

1. A beverage composition to be ingested by a patient prior to administration of anesthesia or sedation comprising:
 a) one or more carbohydrates, wherein the total Calories available from the carbohydrates is at least about 200 and wherein the one or more carbohydrates are the sole source of significant Calories in the beverage;
 b) an acid, in a quantity sufficient to result in a pH of at least about 3.7 to about 4.5;
 c) a central nervous system (CNS) stimulant that is also a cerebro-vasoconstrictor;
 d) a sweetener; and
 e) water,
wherein the beverage composition, when ingested at least about two hours prior to administration of anesthesia or sedation is effective to relieve one or more symptoms associated with prolonged fasting.

2. The beverage composition of embodiment 1, wherein the CNS stimulant is caffeine.

3. The beverage composition of embodiment 1 or 2, comprising L-theanine.

4. The beverage composition of any one of embodiments 1-3, comprising L-citrulline.

5. The beverage composition of any one of embodiments 2-4, wherein the caffeine is in the amount of about 50 mg/serving to about 100 mg/serving.

6. The beverage composition of any one of embodiments 3-5, wherein the L-theanine is in the amount of about 100 mg/serving to about 200 mg/serving.

7. The beverage composition of any one of embodiments 4-6, wherein the L-citrulline is in the amount of about 3 mg/serving to about 6 mg/serving.

8. The beverage composition of any one of embodiments 1-7, comprising an aspiration prophylaxis.

9. The beverage composition of embodiment 8, wherein the aspiration prophylaxis is a selective serotonin 5HT3 receptor antagonist and/or a dopamine-receptor antagonist.

10. The beverage composition of any one of embodiments 1-9, comprising at least one health-enhancing agent.

11. The beverage composition of embodiment 10, wherein the at least one health-enhancing agent is selected from the group consisting of an herbal medicament, a vitamin, a mineral and an amino acid.

12. The beverage composition of any one of embodiments 1-11, comprising at least one flavor-enhancing agent.

13. The beverage composition of embodiment 12, wherein the at least one flavor-enhancing agent is selected from the group consisting of peppermint, spearmint, cinnamon, fruit flavoring, coffee flavoring, tea flavoring, comfrey, licorice, vanilla, ginger and vegetable flavoring (e.g., kale, etc.).

14. The beverage composition of any one of embodiments 1-13, wherein the one or more carbohydrates are selected from the group consisting of dextrose, maltodextrin, fructose, glucose, maltose, sucrose, cellobiose, lactose, sucralose, iso-maltulose, trehalose, and *Stevia Rebaudiana*.

15. The beverage composition of any one of embodiments 1-14, the sweetener is selected from a natural source such as *Stevia Rebaudiana* or a manufactured source, such as aspartame, saccharin and sucralose.

16. The beverage composition of any one of embodiments 1-15, wherein the acid is selected from the group consisting of citric acid and malic acid.

17. The beverage composition of any one of embodiments 1-16, comprising about 44 grams maltodextrin, about 6 grams crystalline fructose, about 0.5 gram citric acid and about 0.5 gram malic acid per serving.

18. The beverage composition of any one of embodiments 1-17, comprising about 0.2 gram of sodium as sodium citrate per serving.

19. The beverage composition of any one of embodiments 1-18, comprising about 0.05 gram of potassium as potassium monophosphate per serving.

20. The beverage composition of any one of embodiments 1-19, comprising about 5 mg of zinc as zinc sulfate per serving.

21. The beverage composition of any one of embodiments 1-20, comprising about 7 mcg of selenium as sodium selenite per serving.

22. The beverage composition of any one of embodiments 1-21, comprising about 0.05 mg of *Stevia Rebaudiana* per serving.

23. The beverage composition of any one of embodiments 1-22, comprising about 2,500 IU of vitamin A per serving.

24. The beverage composition of any one of embodiments 1-23, wherein the beverage composition has a pH of at least about 3.7 to about 4.5.

25. A method of preparing a patient for induction of anesthesia or sedation comprising the steps of:
a) providing an instruction to a patient to fast from solid foods and all non-clear liquids beginning at least about 6 hours prior to the induction;
b) informing the patient to ingest at least one serving of a beverage composition of any one of embodiments 1-24 at least about 2 hours prior to the induction;
c) confirming that the patient has fasted from all food and all liquids following ingestion of the beverage composition; and
d) confirming patient's compliance with the instruction to ingest the final serving of beverage at about two hours prior to procedure.

26. The method of embodiment 25, comprising causing the patient to ingest at least two servings of the beverage composition in two hours intervals, wherein the final ingestion occurs at least 2 hours prior to surgery.

27. The method of embodiment 25 or 26, comprising causing the patient to ingest the beverage composition for at least three servings, including a serving at about 10 hours to about 12 hours prior to surgery, a serving at about 6 hours to about 8 hours prior to surgery; and a serving at least about 2 hours prior to surgery.

28. A beverage container comprising a serving of the beverage composition of any one of embodiments 1-24.

29. The container of embodiment 28, wherein the beverage container comprises a cap label that provides instructions for recording and initialing the actual ingestion time of the beverage composition, and delivery to pre-operative personnel on admission to surgical facility, thus validating the time of the last fluid ingestion.

30. A method of preparing a patient for induction of anesthesia or sedation comprising the steps of:
a) presenting the patient with a beverage container of embodiment 29;
b) causing the patient to fast from solid foods and all non-clear liquids beginning about 6 hours prior to the induction and to ingest only clear liquids without any aspiration prophylaxis or antacid during the first 4 hours of the 6 hour period;
c) causing the patient to ingest at least one serving of a beverage composition of any one of embodiments 1-24 at least about 2 hours prior to the induction;
d) causing the patient to record and initial the ingestion time(s) of the beverage composition; and
e) thereafter causing the patient to also refrain from ingesting all liquids and solids following ingestion of the beverage composition, which is aided by the beverage composition ingestion having satisfied the patient's potential hunger and thirst.

31. A powdered composition comprising the ingredients of the beverage composition of any one of embodiments 1-24 without water.

32. The powdered composition of embodiment 31, comprising about 60 gm of the ingredients per serving.

33. A method for rehydrating the powdered composition of embodiment 31 or 32, wherein the powdered composition is to be rehydrated with water.

34. The method of embodiment 33, wherein the water is from a tap, previously bottled, and/or filtered.

35. The method of embodiment 33 or 34, wherein the water is still or carbonated.

36. The method of any one of embodiments 33-35, wherein the water is chilled or at room temperature.

37. A water-based frozen composition comprising the ingredients of the beverage composition of any one of embodiments 1-24.

DETAILED DESCRIPTION

Formulation of Pre-Operative Beverage Compositions

In one aspect, provided herein are beverage compositions to be ingested by a patient prior to administration of anesthesia or sedation comprising: a) one or more carbohydrates, wherein the total Calories available from the carbohydrates is at least about 200 and wherein the one or more carbohydrates are the sole source of significant Calories in the beverage; b) an acid, in a quantity sufficient to result in a pH of at least about 3.7 to about 4.5 and to enhance the shelf life of the beverage; c) a central nervous system (CNS) stimulant that is also a cerebro-vasoconstrictor; d) a sweetener and e) water, wherein the beverage composition, when ingested at least about two hours prior to administration of anesthesia or sedation is effective to relieve one or more symptoms associated with prolonged fasting or the "starved state." In some embodiments, the beverage composition may include a non-essential amino acid; an electrolyte; a vitamin; and/or a flavoring. In some embodiments, the beverage composition may include an amino acid such as citrulline, arginine, ornithine, etc.

The pre-operative beverage compositions disclosed herein are designed to be administered to a patient prior to surgery or invasive diagnostic procedure to reduce the risk of multiple pre-operative, intra-operative and post-operative complications associated with a prolonged pre-operative fast, including the noxious pre-operative symptoms of thirst, hunger, nausea and generalized discomfort, the intra-operative signs of dehydration and starvation, including difficult intravenous access, hypotension, and the post-operative incidence of nausea and vomiting, insulin resistance with resulting hyperglycemia and infections, especially of surgical wounds.

A pre-operative beverage composition was previously described in U.S. Pat. No. 6,069,131, the content of which is herein expressly incorporated by reference in its entirety. Documented benefits of a single serving of the beverage composition at least two hours prior to surgery include enhanced patient comfort (Crenshaw et al) and other beneficial effects. When compared to patients who were traditionally fasted from midnight before surgery, patients who ingested the beverage composition were 5.5-6.5 times more likely to describe themselves as comfortable. Thirst, hunger, anxiety about fasting and surgery, and nausea were also significantly reduced in patients who had the beverage composition.

Without being bound by a particular theory, it is believed that an additional desirable effect of the pre-operative beverage composition is to prevent a common physiologic response to deprivation of habitually consumed morning beverages that contain a CNS stimulant such as caffeine; such deprivation or "withdrawal" is believed to be responsible for the occurrence of the common headache as well as migraines in both the pre-operative and the post-operative period. See, e.g., Fennelly, Galletly & Perdie; Shapiro; Nikolajsen, Larsen & Kierkegaard. Therefore, in some embodiments, the CNS stimulant caffeine, a crystalline xanthine, may be included in the beverage composition.

The amount of caffeine included in the beverage composition may vary. For example, the amount of caffeine included in the beverage composition may be from about 1 mg to about 1 g or more per serving. In some embodiments, the amount of caffeine included in the beverage composition may be about 1 mg, about 2 mg, about 3 mg, about 4 mg, about 5 mg, about 6 mg, about 7 mg, about 8 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 200 mg, about 300 mg, about 400 mg, about 500 mg, about 600 mg, about 700 mg, about 800 mg, about 900 mg, about 1 g, or a range between any two of these values, per serving. In some embodiments, the amount of caffeine included in the beverage composition may be from about 50 mg to about 100 mg per serving.

Caffeine of any source may be included in the pre-operative beverage composition disclosed herein. For example, caffeine may be a "natural (herbal)" product, or a manufactured or synthesized product.

L-theanine is a non-protein amino acid that crosses the blood brain barrier. It is known to reduce psychological and physiological stress responses (Kimura, Ozeki, Juneia & Ohira). It is also known to work synergistically with caffeine by inhibiting or attenuating its stimulation of the CNS when used in combination (Kakuda, Nozawa, Unno et al). It has been described as a "relaxing agent without sedation", increasing alpha waves of EEG. (Juneja, Chu, Okubo, et al. Therefore, in some embodiments, the pre-operative beverage compositions disclosed herein may comprise L-theanine.

The amount of L-theanine included in the beverage composition may vary. For example, the amount of L-theanine included in the beverage composition may be from about 10 mg to about 1 g or more per serving. In some embodiments, the amount of L-theanine included in the beverage composition may be about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 300 mg, about 400 mg, about 500 mg, about 600 mg, about 700 mg, about 800 mg, about 900 mg, about 1 g, or a range between any two of these values, per serving. In some embodiments, the amount of L-theanine included in the beverage composition may be from about 100 mg to about 200 mg per serving.

L-theanine of any source may be included in the pre-operative beverage composition disclosed herein. For example, L-theanine may be a natural product (e.g., purified from green tea) or a manufactured or synthesized product.

L-citrulline is a non-protein, non-essential amino acid. It is one of three dietary amino acids, including L-arginine and L-ornithine, that are critical in the urea and nitric oxide cycles. L-citrulline is an important participant in the nitric oxide (NO) cycle, boosting levels of this important vasodilator and anti-hypertensive. It has been shown that oral ingestion increases critical L-arginine pools (plasma and muscle) and restores nitrogen balance associated with the catabolic state more effectively than oral L-arginine supplementation (Schwedhelm, Maas, Freese, et al). Its conversion occurs in the kidneys (Osowska, Moinard, Neveux, et al). L-citrulline is produced exclusively by enterocytes from glutamine. Plasma levels of L-citrulline are decreased on average by 60% in critically ill ICU patients; such decreases in non-ICU patients with "short bowel syndrome" reflect severe loss of enterocyte mass (cells) (Peters, Beishuizen, Keas et al). L-citrulline plays a key role in the immune function of bowel wall enterocytes. Unlike oral administration of L-arginine that is associated with diarrhea and other systemic side-effects, short-term oral L-citrulline is safe and well tolerated with optimal daily intake being 10 grams (Curis, Nicolis, Moinard, et al; Moinard, Nicolis, Neveux, et al). Low levels of L-citrulline are associated with acute respiratory distress (Ware, Magarik, Wickersham, et al). It has been suggested that L-citrulline is not only a critical biomarker of reduction of functional enterocyte (bowel) functional mass but also a "conditionally essential" versus a non-essential amino acid and pharmaco-nutrient in critically ill patients (Cynober). Therefore, in some embodiments, the pre-operative beverage compositions disclosed herein may comprise L-citrulline.

The amount of L-citrulline included in the beverage composition may vary. For example, the amount of L-citrulline included in the beverage composition may be from about 1 mg to about 4 g or more per serving. In some embodiments, the amount of L-citrulline included in the beverage composition may be about 1 mg, about 2 mg, about 3 mg, about 4 mg, about 5 mg, about 6 mg, about 7 mg, about 8 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 200 mg, about 300 mg, about 400 mg, about 500 mg, about 600 mg, about 700 mg, about 800 mg, about 900 mg, about 1 g, about 2 g, about 3 g, about 4 g, or a range between any two of these values, per serving. In some embodiments, the amount of L-citrulline included in the beverage composition may be from about 3 mg to about 6 mg per serving.

L-citrulline of any source may be included in the pre-operative beverage composition disclosed herein. For example, L-citrulline may be a natural product (e.g., purified from watermelon and some other members of the melon/squash family) or a manufactured or synthesized product.

In some embodiments, dextrose or sucrose may be used as a substitute for crystalline fructose to reduce sweetness of the pre-operative beverage.

Some embodiments provided herein relate to beverage compositions which may be ingested at least about 2 hours prior to administration of anesthesia or sedative/analgesia by a patient for scheduled surgery. Some of the desirable properties of the pre-operative beverage compositions disclosed herein are that they are readily absorbed in the stomach and the small intestine, thereby delivering energy and fluid to the intracellular space; that they are well tolerated by the patient without causing GI distress; that they alleviate thirst and hunger associated with prolonged fasting by the patient, and that they restore the patient's metabolism from the "starved" to the "fed" state, thereby reactivating the important glucose-insulin metabolic relationship that is key to overcoming the additional stress of surgery.

In some embodiments, the pre-operative beverage composition disclosed herein may be able to deliver at least about 200 Calories of energy to the patient per serving. The serving size of the pre-operative beverage composition may vary. For example, a single serving may have a size of about 6 oz, about 8 oz, about 10 oz, about 12 oz, about 16 oz, about 18 oz, about 20 oz, or more. It is also important that the beverage composition have an osmolarity within that of the normal physiological range, and most preferably an osmolarity of about 265 mosm to about 300 mosm.

In some embodiments, the pre-operative beverage composition disclosed herein may include zinc as zinc sulfate (about 5 mg) and selenium as sodium selenite (about 7 mcg) per serving. The pre-operative beverage composition disclosed herein may include a carbohydrate source such as dextrose, M040 maltodextrin, M100 maltodextrin, M150 maltodextrin, M180 maltodextrin, fructose, glucose, maltose, sucrose, cellobiose and lactose, sucralose, iso-maltulose, trehalose and *Stevia Rebaudiana*, etc., or a combination thereof. In some embodiments, the pre-operative beverage composition disclosed herein may include a sweetener such as *Stevia Rebaudiana* (natural) and artificial sources such as aspartame, saccharin, sucralose, etc. without increasing the osmolarity. In some embodiments, the pre-operative beverage composition disclosed herein may include naturally occurring glycoside *Stevia Rebaudiana* at about 0.05 mg per serving. In some embodiments, the pre-operative beverage composition disclosed herein may include about 44 gm maltodextrin, about 6 gm crystalline fructose, about 0.5 gm citric acid and about 0.5 gm malic acid per serving. In some embodiments, the pre-operative beverage composition disclosed herein may have a pH of at least about 3.7 to about 4.5. In some embodiments, the pre-operative beverage composition disclosed herein may include about 2,500 IU of vitamin A per serving.

Further provided herein are powdered compositions comprising the ingredients of the beverage compositions disclosed herein without water. In some embodiments, the powdered compositions may be rehydrated to produce a like beverage by the addition of about 12 oz of water with that water being from a tap, previously bottled (filtered or otherwise), still or carbonated (naturally or otherwise), chilled or at room temperature.

Beverage Container

Further provided herein are beverage containers that may comprise a serving of the beverage compositions disclosed herein. The beverage containers may be of various sizes and shapes. For example, the size of the beverage containers may be suitable for a serving size of about 6 oz, about 8 oz, about 10 oz, about 12 oz, about 16 oz, about 18 oz, about 20 oz, or more.

In some embodiments, the beverage containers may comprise a label that provides instructions for recording and initialing the actual ingestion time of the beverage composition. The label may be located on any part of the beverage container that is readily accessible to a patient. For example, the label may be on the side of the beverage container or, preferably, on the cap of the beverage container. In some embodiments, the label may be in compliance with the latest recommendation of the ASA® for validation of a patient's clear liquid ingestion time. In some embodiments, the label may provide for recording and initialing the actual ingestion time of the pre-operative beverage composition. In some embodiments, the label may comprise instructions to the patient to bring the cap to the pre-operative admissions personnel for validation of their correct fasting time.

Methods of Using the Pre-Operative Beverage Compositions

In another aspect, provided herein are methods of using the pre-operative beverage compositions disclosed herein in preparation for the induction of anesthesia or sedation in a patient before surgery. In some embodiments, the methods provided herein may comprise: a) causing the patient to fast from solid foods and all non-clear liquids beginning at least about 6 hours prior to the induction; b) causing the patient to ingest at least one serving of a beverage composition disclosed herein at least about 2 hours prior to the induction; c) causing the patient to fast from all food and all liquids following ingestion of the beverage composition. In some embodiments, the pre-operative beverage compositions disclosed herein may be used to prevent dehydration and starvation in a patient and/or to sustain optimal insulin and glucose levels and interactions in a patient.

A person of ordinary skill in the art should be able to recognize that the pre-operative beverage compositions may be ingested by a patient according to a variety of schedules. For example, the pre-operative beverage compositions disclosed herein may be ingested by a patient in at least one serving at least 2 hours prior to surgery. In some embodiments, the pre-operative beverage compositions disclosed herein may be ingested by a patient for at least one, at least two, or at least three servings within the 12 hours prior to surgery with the last serving being consumed at least 2 hours prior to surgery.

In some embodiments, the pre-operative beverage compositions disclosed herein may be ingested by a patient in at least three servings, a first serving at about 10 hours to about 12 hours prior to surgery, a second serving at about 6 hours to about 8 hours prior to surgery; and a third serving at least about 2 hours prior to surgery.

In some embodiments, the methods disclosed herein may include presenting the patient with a beverage container which comprises a cap label that provides instructions for recording and initialing the actual ingestion time of the beverage composition, and delivery to pre-operative personnel on admission to surgical facility, thus validating the time of the last fluid ingestion. In some embodiments, the methods disclosed herein may comprise causing the patient to record and initial the ingestion time(s) of the beverage composition. This facilitates the pre-operative staff's verification of patients' compliance with the terms of the pre-operative fasting instructions on reviewing the endorsed cap label.

In some embodiments, the methods disclosed herein may be used in compliance with the ERAS® Protocol. For example, the pre-operative beverage compositions disclosed herein may be ingested by a patient for at least two, at least three or more servings in two to six hours intervals, wherein the final ingestion occurs at least 2 hours prior to surgery. The pre-operative beverage compositions and methods of treatment disclosed herein may contribute to the Protocol's favorable impact on surgical outcomes in the following ways:

1. Reduces post-operative insulin resistance (PIR);
2. Reduces post-operative hyperglycemia that is the result of PIR;
3. Reduces post-operative wound infections and other complications, including PONV; and
4. Reduces post-operative length of stay (LOS) in and re-admissions to hospitals.

EXAMPLES

Additional embodiments are disclosed in further detail in the following examples, which are not in any way intended to limit the scope of the claims.

Example 1

Expanded recommended schedule of ingestion for non-ERAS® Protocol patients.

A minimum of one serving is ingested at least 2 hours prior to surgery. In the event of a substantial delay in the surgery schedule, it is advised that one or more additional servings be ingested, in two hours intervals, so long as the final serving occurs at least 2 hours prior to surgery.

Example 2

Expanded recommended schedule of ingestion for ERAS® Protocol patients.

A minimum of three suggested servings are ingested instead of one:
  a. One serving at about 12 hours prior to surgery;
  b. A second serving at about 8 hours prior to surgery;
  c. A third serving at least 2 hours prior to surgery.

Again, if there is an unforeseen delay in the surgery schedule, it is strongly recommended that one or more servings be ingested, in two-hour intervals, so long as the final serving occurs at least 2 hours prior to surgery to accomplish the above goals.

Example 3

Method of manufacturing the pre-operative beverage composition.

Batching: measured amounts of dry components and liquid flavorings are sterilely combined in a vat with calculated volume of water. Citric acid, malic acid and sodium citrate are added in amounts appropriate to adjust the overall pH of the beverage to a range of ≥3.7-4.5.

Hot fill vs. aseptic/pasteurization process:
  a. The "hot-fill" sterilization process that limits the beverage heating process to 185° F. is used for the sterilization process;
  b. An aseptic or pasteurization process that raises the beverage temperature to 203° F. before instant cooling is an alternative sterilization option.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

REFERENCES

1. Lassen K, Soop M, Nygren J, et al. Consensus Review of Optimal Peri-operative Care in Colorectal Surgery. Enhanced Recovery After Surgery (ERAS) Group Recommendations. JAMA Surgery, 2009; 144(10):961-969
2. Fearon K C L, Ljungqvist O, Von Meyenfeldt M, et al. Enhanced recovery after surgery: a consensus review of clinical care for patients undergoing colonic resection. Clin Nutr, 2005; 24(3):466-477
3. Ljungqvist O. Jonathan Woods Lecture 2011: Insulin Resistance and enhanced recovery after surgery. J Parent Ent Nutr, 2012:36(4):389-98
4. Yagmurdur H, Gunal S, Yildiz H, et al. The effects of carbohydrate-rich drinks on peri-operative discomfort, insulin response and arterial pressure in spinal anesthesia. J Res Med Sci, 2011; 10(11):1483-89
5. Jones C, Badger S A, Hannon R. The role of carbohydrate drinks in pre-operative nutrition for elective colorectal surgery. Ann R Coll Surg Engl, 2011; 93(7):504-07
6. Tamura T, Tomoaki Y, Hiroyuki K, et al. Oral carbohydrate loading with 18% carbohydrate beverage alleviates insulin resistance. Asia Pac J Clin Nutr, 2013; 22:48-53
7. Crenshaw J T, Mischke A, Gilder R E. The effects of a prescribed pre-operative carbohydrate-rich liquid beverage on elective surgery patients' ratings of discomfort from prolonged fasting. Abstract, 27$^{th}$ Annual Meeting of Society for Ambulatory Anesthesia, 2012, Miami, Fla.
8. Fennelly M, Galletly D C, Purdie G I. Is caffeine withdrawal the mechanism of post-operative headache? Anesth Analg 1991; 72(4):449-53
9. Shapiro R E. Caffeine and headaches. Curr Pain Headache Rep. 2008; 12(4):311-5
10. Nikolajsen L, Larsen K M, Kierkegaard O. Effect of previous frequency of headache, duration of fasting and caffeine abstinence on peri-operative headache. Br J Anaesth. 1994; 72(3):295-7
11. Kimura K, Ozeki M, Juneja L R, Ohira H. L-Theanine reduces psychological and physiological stress responses. Biol Psychol. 2007; 74(1):39-45
12. Kakuda T, Nozawa A, Unno T, et al. Inhibiting effects of theanine on caffeine stimulation evaluated by EEG in the rat. Biosci Biotechnol Biochem 2000; 64:287-93
13. Juneja L R, Chu D-C, Okubo, T, et al. L-theanine—a unique amino acid of green tea and its relaxation effects in humans. Trends Food Sci & Tech, 1999; 10:199-204
14. Schwedhelm E, Maas R, Freese R, et al. Pharmacokinetic and pharmacodynamic properties of oral L-citrulline and L-arginine: impact on nitric oxide metabolism. Br J Clin Pharmacol, 2007; 65(1):51-59
15. Osowska S, Moinard C, Neveux N, e al. Citrulline increases arginine pools and restores nitrogen balance after massive intestinal resection. Gut, 2004; 53:1781-6
16. Peters J H, Beishuizen A, Keur M B, et al. Assessment of small bowel function in critical illness: potential role of citrulline metabolism. J Intensive Care Med, 2011; 26:105-10
17. Moinard C, Nicolis I, Neveux N, et al. Dose-ranging effects of citrulline administration on plasma amino acids and hormonal patterns in healthy subjects: the Citrulose pharmacokinetic study. Br J Nutr, 2008; 99:855-62
18. Ware L B, Magarik J A, Wickersham N, et al. Low plasma citrulline levels are associated with acute respiratory distress syndrome in patients with severe sepsis. Crit Care, 2013; 17:R10
19. Cynober L. Citrulline: just a biomarker or a conditional essential amino acid and a pharmaconutrient in critically ill patients? Crit Care 2013; 17:122

What is claimed is:
1. A method of administering a pre-operative clear beverage composition to a patient prior to anesthesia or sedation, the method comprising:
   identifying a patient scheduled for surgery or sedation; and
   administering to the patient at least one serving of a clear and colorless pre-operative beverage composition comprising one or more carbohydrates and L-citrulline at least two hours prior to the surgery or sedation.
2. The method of claim 1, wherein the L-citrulline is present in the amount of 1 g/serving to 4 g/serving.
3. The method of claim 1, wherein the one or more carbohydrates comprise maltodextrin or sucrose.

4. The method of claim 3, wherein the one or more carbohydrates comprise maltodextrin in an amount of 44 grams per serving.

5. The method of claim 1, wherein the pre-operative beverage composition further comprises a central nervous system (CNS) stimulant.

6. The method of claim 5, wherein the CNS stimulant comprises caffeine.

7. The method of claim 6, wherein the pre-operative beverage composition CNS stimulant comprises caffeine in an amount of 50 mg/serving to 100 mg/serving.

8. The method of claim 1, wherein the pre-operative beverage composition further comprises a sweetener.

9. The method of claim 8, wherein the sweetener comprises *Stevia*.

10. The method of claim 9, wherein the sweetener comprises *Stevia* in an amount of about 0.05 mg per serving.

11. The method of claim 1, wherein the pre-operative beverage composition further comprises an acid selected from the group consisting of citric acid and malic acid.

12. The method of claim 11, wherein the pre-operative beverage composition comprises citric acid and maltodextrin, and the ratio of citric acid to maltodextrin in the pre-operative beverage composition is about 1:88 or greater.

13. The method of claim 1, wherein the pre-operative beverage composition has an osmolarity of 265 milliosmole to 300 milliosmole.

14. The method of claim 1, wherein the pre-operative beverage has a pH of at least 3.7.

15. The method of claim 1, wherein administering to the patient at least one serving comprises administering to the patient a first serving and a second serving of the pre-operative beverage composition, and the second serving is administered within two hours of the first serving.

16. The method of claim 15, wherein the second serving is administered at least 2 hours prior to the surgery or sedation.

17. The method of claim 1, wherein the pre-operative beverage composition further comprises L-theanine.

18. The method of claim 1, wherein one serving of the pre-operative beverage composition comprises 12 fluid ounces of the pre-operative beverage composition.

19. The method of claim 1, wherein administering to the patient at least one serving comprises administering to the patient a first serving, a second serving and a third serving of the pre-operative beverage composition, wherein the first serving is administered at 10 hours to 12 hours prior to surgery, the second serving is administered at 6 hours to 8 hours prior to surgery, and the third serving is administered at least 2 hours prior to surgery.

20. The method of claim 1, further comprising causing the patient to fast from solid foods and all non-clear liquids beginning about 6 hours prior to the administration of the pre-operative beverage composition.

\* \* \* \* \*